United States Patent
Daffer et al.

(12) 
(10) Patent No.: US 6,623,511 B1
(45) Date of Patent: Sep. 23, 2003

(54) CHROMATHERAPY SHOWER SYSTEM

(75) Inventors: Steven J. Daffer, Edina, MN (US); Richard W. Jostrom, Mound, MN (US); Georgios Mertikas, Edina, MN (US)

(73) Assignee: Visibelle Derma Institute, Inc., Bloomington, MN (US)

( * ) Notice: Subject to any disclaimer, the term of this patent is extended or adjusted under 35 U.S.C. 154(b) by 158 days.

(21) Appl. No.: 09/706,946

(22) Filed: Nov. 6, 2000

Related U.S. Application Data

(63) Continuation-in-part of application No. 09/690,317, filed on Oct. 17, 2000, now Pat. No. 6,497,717, which is a continuation-in-part of application No. 09/289,628, filed on Apr. 12, 1999, now abandoned.

(51) Int. Cl.[7] ......................... A61H 21/00; A61H 33/00
(52) U.S. Cl. ..................... 607/82; 607/81; 607/83; 607/88; 128/898; 4/524; 4/529; 4/597; 4/601
(58) Field of Search ..................... 607/80–82, 87–89; 128/898; 4/524–534, 596–611

(56) References Cited

U.S. PATENT DOCUMENTS

| | | |
|---|---|---|
| 1,059,314 A | 4/1913 | Petter |
| 1,643,528 A * | 9/1927 | Thurston .................. 607/80 |
| 1,797,916 A | 3/1931 | Kruse |
| 2,012,221 A | 8/1935 | Clark et al. |
| 2,096,128 A | 10/1937 | Mortrude, Jr. |
| 2,240,819 A | 5/1941 | Waly |
| 2,300,455 A | 11/1942 | Lukats |
| 2,567,614 A * | 9/1951 | Merriam .................. 607/82 |
| D189,951 S | 3/1961 | Cosper |
| 3,409,915 A | 11/1968 | Jauvais |
| 3,772,713 A | 11/1973 | Roullier |
| 3,945,058 A | 3/1976 | Gardner |
| 4,031,573 A | 6/1977 | Romanoff |
| 4,055,863 A | 11/1977 | Duval |
| D249,894 S | 10/1978 | Brancaccio et al. |
| 4,130,120 A | 12/1978 | Kohler, Jr. |
| D255,491 S | 6/1980 | Brancaccio et al. |
| 4,258,706 A | 3/1981 | Shank |
| 4,277,855 A | 7/1981 | Poss |
| D275,605 S | 9/1984 | Taylor |
| 4,565,188 A | 1/1986 | Hardie |
| 4,671,284 A | 6/1987 | Wilson et al. |
| 4,712,538 A | 12/1987 | Hardie et al. |

(List continued on next page.)

FOREIGN PATENT DOCUMENTS

| | | |
|---|---|---|
| DE | 725804 | 3/1944 |
| DE | 3915008 A1 | 11/1990 |
| EP | WO 00/02491 | 1/2000 |
| EP | 0 986 985 A1 | 3/2000 |
| FR | 2086905 | 12/1971 |
| FR | 2629343 | 10/1989 |
| FR | 2 803 512 | 7/2001 |
| GB | 1490381 | 11/1977 |
| JP | 8112302 | 5/1996 |

*Primary Examiner*—David M. Shay
(74) *Attorney, Agent, or Firm*—Westman, Champlin & Kelly, P.A.

(57) ABSTRACT

A personalized therapeutic compartment includes a horizontal bed for supporting a person to be treated, and has a shower system with a plurality of shower nozzles arrayed above the bed so that a person can have a therapeutic shower while lying on the bed. The shower system includes a water source which may be colored and coordinated with a light source on the interior of the compartment. A source of aroma is provided that suggests the color used for total therapy treatment. Additional therapeutic steam and dry air can be provided as desired. A method of treatment disclosed includes chromatherapy using coordinated colors and aroma and if desired requested colors for therapy of different portions of the body of a user.

22 Claims, 8 Drawing Sheets

U.S. PATENT DOCUMENTS

| | | |
|---|---|---|
| 4,833,739 A | 5/1989 | Sakakibara et al. |
| 4,862,526 A | 9/1989 | Berger |
| 4,884,574 A | 12/1989 | Hardie et al. |
| 5,101,809 A | 4/1992 | Daffer et al. |
| 5,255,399 A | 10/1993 | Park |
| 5,416,931 A | 5/1995 | Wolfenden et al. |
| D360,469 S | 7/1995 | Panelli et al. |
| 5,441,529 A | 8/1995 | Dorsch |
| 5,511,254 A | 4/1996 | O'Brien |
| 5,546,678 A | 8/1996 | Dhaemers |
| 5,645,578 A * | 7/1997 | Daffer et al. .................. 607/88 |
| 6,004,344 A | 12/1999 | Fujii |
| 6,021,960 A * | 2/2000 | Kehat ......................... 239/289 |

\* cited by examiner

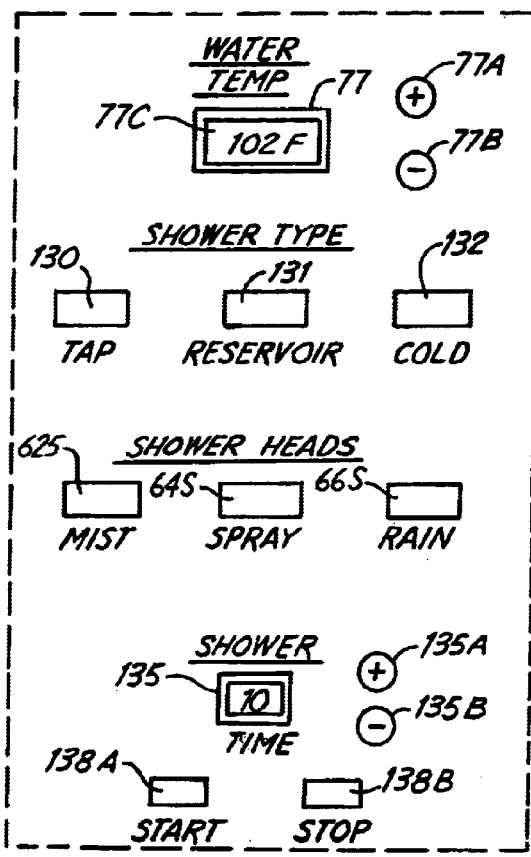
FIG. 6A
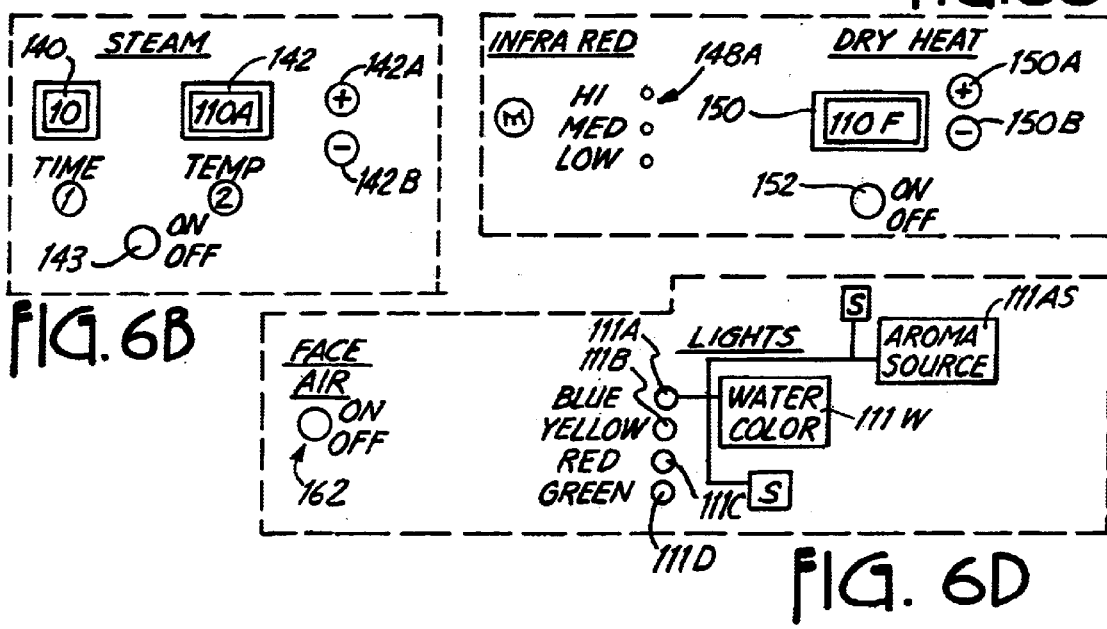
FIG. 6B
FIG. 6C
FIG. 6D

CHROMATHERAPY SHOWER SYSTEM

CROSS REFERENCE TO RELATED APPLICATION

This application is a continuation-in-part of U.S. patent application Ser. No. 09/690,317, filed Oct. 17, 2000 now U.S. Pat. No. 6,497,717 for Therapy steam and Heat Treatment Cabinet, which in turn was a continuation-in-part of U.S. patent application Ser. No. 09/289,628, filed Apr. 12, 1999 now abandoned for THERAPY STEAM AND HEAT TREATMENT both of which are fully incorporated herein by reference.

BACKGROUND OF THE INVENTION

The present invention relates to a therapy system for a personalized capsule that will provide for various therapies including showering, heat, air drying, steam, chromatherapy, and aroma therapy for a person lying on an interior bed. The color of the light is selected to be compatible with the desired therapy, and like colored shower water is used when desired for total chromatherapy treatment. Aroma coordinated with the color can be provided. Heat, steam and air drying can be used as desired.

Personalized environmental capsules in which a person can lie on a bed, and be treated with heat, vibration, and various light therapies have been advanced. U.S. Pat. Nos. 5,101,809 and 5,645,578 illustrate therapeutic compartments, which have gained wide popularity for individual treatment.

In the above-identified cross referenced applications, the addition of steam has been made, with various improvements in utilizing a horizontal bed and enveloping the user in a steam environment, and providing steam outlets directed to the face of the user where desired. However, in order to have a further enhanced therapeutic environment, the various formations of coordinated colors, lights, and aromas have been recognized as helpful.

SUMMARY OF THE INVENTION

The present invention relates to an individual personalized therapeutic compartment that provides the advantages of a chromatherapy shower treatment system, and includes sources of dry heat and steam. Total chromatherapy and aromatherapy are provided as desired. The aromas are coordinated with the colors that are used for the chromatherapy.

A hydro or shower is provided as a primary function. The water used for the shower may be colored into a desired color, which would be coordinated with interior and, if desired, exterior lights. An aroma that is at least suggestive of the color used in chromatherapy is provided. For example, a yellow color for the lights and shower liquid could be associated with a lemon scent. Green could be associated with lime scent, and orange could be associated with an orange scent. Red could be associated with strawberries or cherries, for example. Lavender or purple could be associated with the fragrance lavender. In this manner, the overall therapeutic environment is coordinated, enhanced, and strengthened.

The present invention includes a structure that has an environmental capsule with shower heads spaced longitudinally along a cover overlying a person lying on the bed. A suitable bed construction is made so that drains or gutters are formed along the sides of the bed. A recirculation pump and filter system can be used for recirculating the water while injecting colors as well as aromas into the water and into the air. Additionally, the housing will have interior lights of different colors, specifically as described, an array of six colors (a rainbow), that can be turned on for chromatherapy radiation as well as having the shower system coordinated as to color of the shower liquid or water, and the coordinated scent for aromatherapy at the same time.

The control panel or divider of the present device, which normally divides the bed or body chamber from the head can have transparent windows so that the person lying on the bed can review the color being applied at the same time the warmth of a shower and the chromatherapy lights can be sensed. For drying, heated air ducts can be utilized for directing warm air over the body for drying and soothing the skin. The water temperature used in the showers can be adjusted as desired, and if desired, steam can also be generated and used during, before or after showering and while heated air is provided, if desired.

The environmental capsule has a central lower chamber that houses the necessary components, and which can be accessed by removing the bed.

The gutters providing drainage are formed along the sides of the bed and slope so water shedding from the waterproof covering of the bed and the body of the person lying on the bed flows into the gutters, and then to drain where it can be recaptured, pumped away, or drained to a waste drain. In short, the overall combination aids in the total therapy treatment and importantly for the first time utilizes an individual compartment with a horizontal bed and shower systems above the body of the user.

The shower system includes three different types of shower heads as shown, and can be provided with adjustable shower heads that will provide a fine mist, a spray or a rain-like shower. The types can be run simultaneously or individually.

In addition, the adjustment for temperature can be made utilizing sensors as well as manual controls, including an anti-scald valve. The system can have a hand-held shower that can be used on the interior of the housing, with the waste being drained as previously explained.

BRIEF DESCRIPTION OF THE DRAWINGS

FIG. 2A is a perspective view of an auxiliary water supply tank used with the present invention;

FIGS. 6A–6D are schematic representations of sections of a control panel and system utilized with the present invention;

DETAILED DESCRIPTION OF THE PREFERRED EMBODIMENTS

Figure 1:
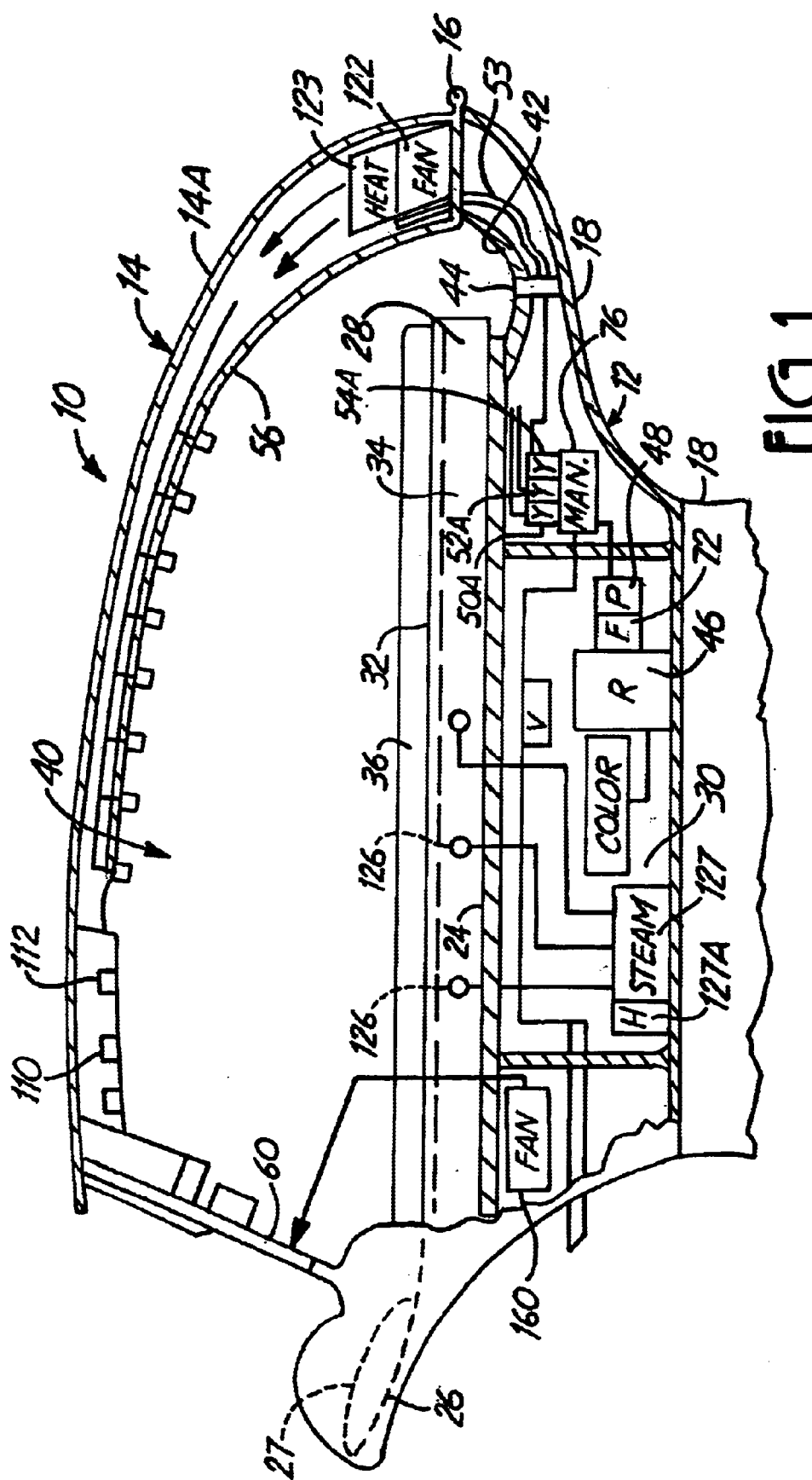
FIG. 1 is a side schematic sectional view of an individual compartment having therapy components made according the present invention.

A chromatherapy shower system capsule indicated generally at 10 includes a base unit 12, and a cover 14 hinged together at a hinged axis 16 at the forward end of the base unit 12. The base unit 12 includes a pedestal 18, and a bed support enclosure or compartment 20 positioned on top of the pedestal 18. The bed support enclosure 20 has a horizontal support wall 22 that extends across the bed support enclosure. The wall 22 has gutters 24, extending longitudinally along the sides of the bed support enclosure. A headrest end indicated at 26 is provided with a suitable pillow for resting the head of a user.

The horizontal support wall 22 of the bed support enclosure 20 supports a rigid channel shaped bed member 28 that forms a shroud overlying an opening providing access to a center cavity 30 below wall 22 that contains the components needed for carrying out the showering, chromatherapy, heating and steam therapy and certain aspects of aroma therapy. The components also can be housed in pedestal 18. The cavity 30 opens upwardly, and the opening is bounded on the sides by the gutters 24. The cavity 30 has closed ends.

The channel shaped bed member 28 includes an upper horizontal support wall 32, and legs 34, which extend downwardly and rest along the sides of the gutters 24 without interfering with the free flow of waste water in the gutters. A cushion 36 is provided on top of the support wall 32, for supporting a person in position. The cushion 36 can be covered with waterproof material, which is necessary when the person is being showered on the interior of the personal compartment or chamber indicated at 40.

The foot end of the compartment 40 has a wall 42 in which a drain opening 44 is provided. The gutters 24 are made so that they slope toward the drain 44. The drain 44 will drain material back into a suitable reservoir indicated generally at 46 that can be used for supply of water for the shower system.

SHOWER SYSTEM

The reservoir 46 has a pump 48 connected thereto with a filter 72 on the pump input line. The pump 48 is operated by suitable control and provides water under suitable pressure, as will be seen schematically, respectively to lines 50, 52 and 54. The lines 50, 52 and 54 provide for three different types of shower nozzles or heads, as shown in the preferred embodiment. Lines 50, 52 and 54 have suitable solenoid valves 50A, 52A and 54A in line leading from a manifold (see FIGS. 1 and 7), so that the lines can be opened and closed as desired. The pump 48 also will have suitable switches or speed controls for controlling it. The lines 50, 52 and 54 have flexible portions carried across the hinge section 16 as shown typically at 53, and are positioned between an outer wall 14A of the cover, and an inner wall or shroud 56. The lines extend along the length of the cover 14 from adjacent the foot end of the bed support compartment 20 to adjacent a divider panel 60 that is provided at the end of the bed support compartment, and out of which the head of the user will extend. The head of the user can be rested on a pillow, as previously explained and which is shown schematically at 27.

Each of the water-shower lines 50, 52 and 54 is provided with a plurality of shower nozzles or heads. As shown, there are mist type shower nozzles or heads 62 connected to the line 50, spray type shower nozzles or heads 64 connected to the line 52, and rain or true sprinkler type shower nozzles or heads 66 connected to the line 54. The lines are deadened, so that when the solenoid valves in the respective line is open, the water will be provided under pressure from the pump 48 through suitable controls and a heater if needed, to provide proper temperature water for the shower.

Figure 7:
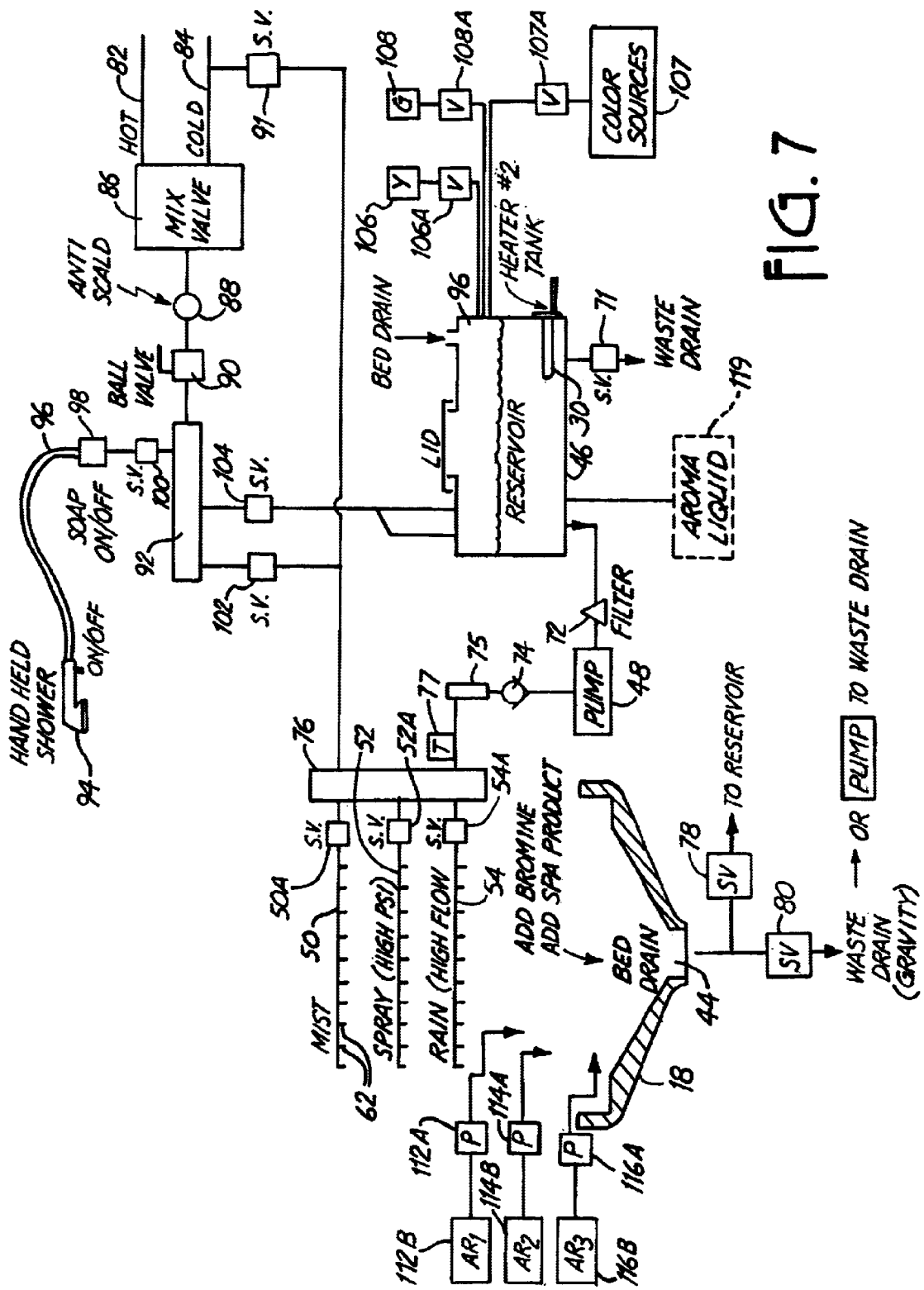
FIG. 7 is a schematic representation of the plumbing system of the present invention.

The schematic representation of the shower system is illustrated in FIG. 7 and it can be seen that the reservoir 46 has a tank heater 70 immersed on the interior. The heater is connected to a suitable source of power. The pump 48 is illustrated schematically, and the high efficient filter 72 is provided on the intake side of the pump. A check valve 74 is provided in the circuit on the output side of the pump 48 to prevent backflow. An inline heater 75 is also provided for final temperature control before providing the water to the manifold. A thermostat 77 in the line from the pump to the manifold can be used to control both heaters 70 and 75 so the water temperature is controlled. The water lines 50, 52 and 54 are connected to a manifold 76, with the solenoid valves 50A, 52A and 54A in circuit as shown in FIG. 7. The reservoir has a drain solenoid valve 71 that can be actuated for cleaning. Disinfectants or various spa products can be added to the water as well.

The bed compartment 40 is also shown schematically in FIG. 7, with the drain 44 in position. Suitable solenoid valves 78 and 80 can be provided from the drain 44 so that the drain 44 will provide water to the reservoir 46 and pump 48 or to the waste drain.

By way of an alternative source of water for the shower, external connections can be provided to the shower lines 50, 52 and 54. Hot and cold water lines 82 and 84 from a tap or home supply, for example or from a mobile tank, and a mixing valve 86 can be used for setting the proper temperature.. A thermostatically controlled anti-scald valve 88 of conventional design is utilized with the external tap where the home source of water is connected, and an on/off valve or ball valve 90 is provided in a flow line to a manifold 92. A cold water bypass solenoid valve 91 controlled through a switch by the user can direct cold water to the manifold 76 and to the shower lines if a cold rinse or cold shower is desired.

A hand-held shower head 94 with a separate on-off valve is connected with a hose 96 through a soap dispenser or injector 98, and a solenoid valve 100 to receive water from the manifold 92. When desired, with manifold output solenoid valves 102 and 104 closed, water can be discharged through the hand-held shower 94 and used by the occupant of the chamber or compartment 49 lying on the bed cushion 36 for cleansing and treating areas of the body that may be shielded from the shower heads. While solenoid valves are described, other valves can be used including manually operated valves. Remotely controlled valves are preferred.

CHROMATHERAPY SYSTEM

The shower system that has been explained and which is connected to tank or reservoir 46 is used as part of a chromatherapy and aroma regiment. Sources of different colors for the shower water are provided. Two sources are shown in FIG. 7 by way of example. A yellow color material source 106 and a green color source 108 are shown in FIG. 7, with sources of orange, red, indigo and other selected colors are represented at 107. These color sources can be various non-toxic liquid coloring, similar to ordinary food coloring, that will hold a sufficient amount of liquid colorant to color the volume of water in the reservoir 46 a desired amount. Dispensing the colorant is controlled through solenoid valves 106A, 107A and 108A, so that the colorant will be discharged positive pressure or drained into the reservoir or tank 46 when the solenoid valves, respectively, are operated. This will color the water. The source of color can be pumped in as well or it can be a powder dispensed when desired. The selection of the color of water will be coordinated with lights from light sources, such a yellow bulb 110 and a green bulb 112, shown in FIGS. 1 and 4. Additional lights 113, 114, 115 and 117 represent red, orange, blue, and indigo or violet (a spectrum of colors).

Figure 4:
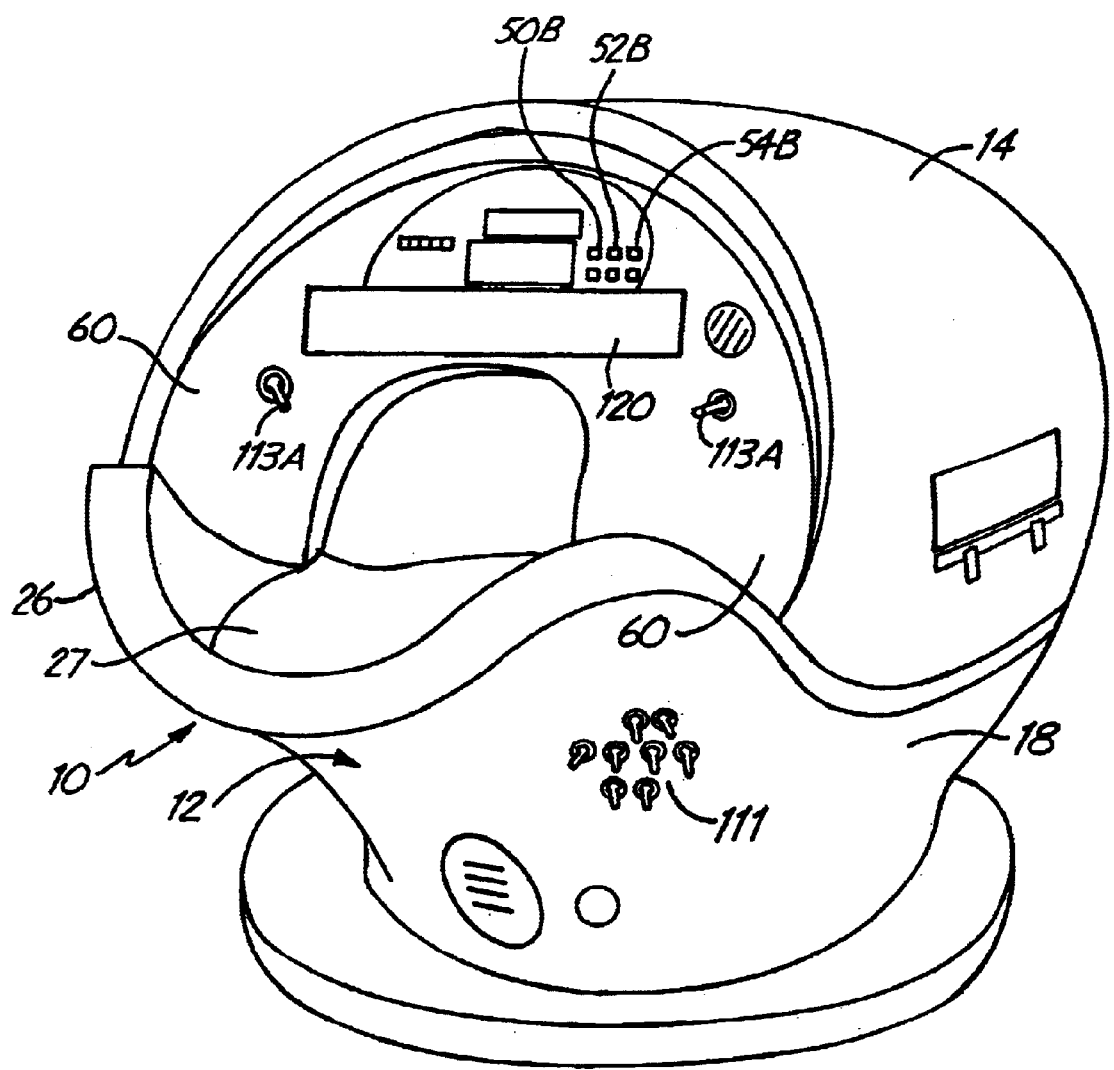
FIG. 4 is a partial perspective view of a divider and control panel assembly made according the present invention.
Figure 5:
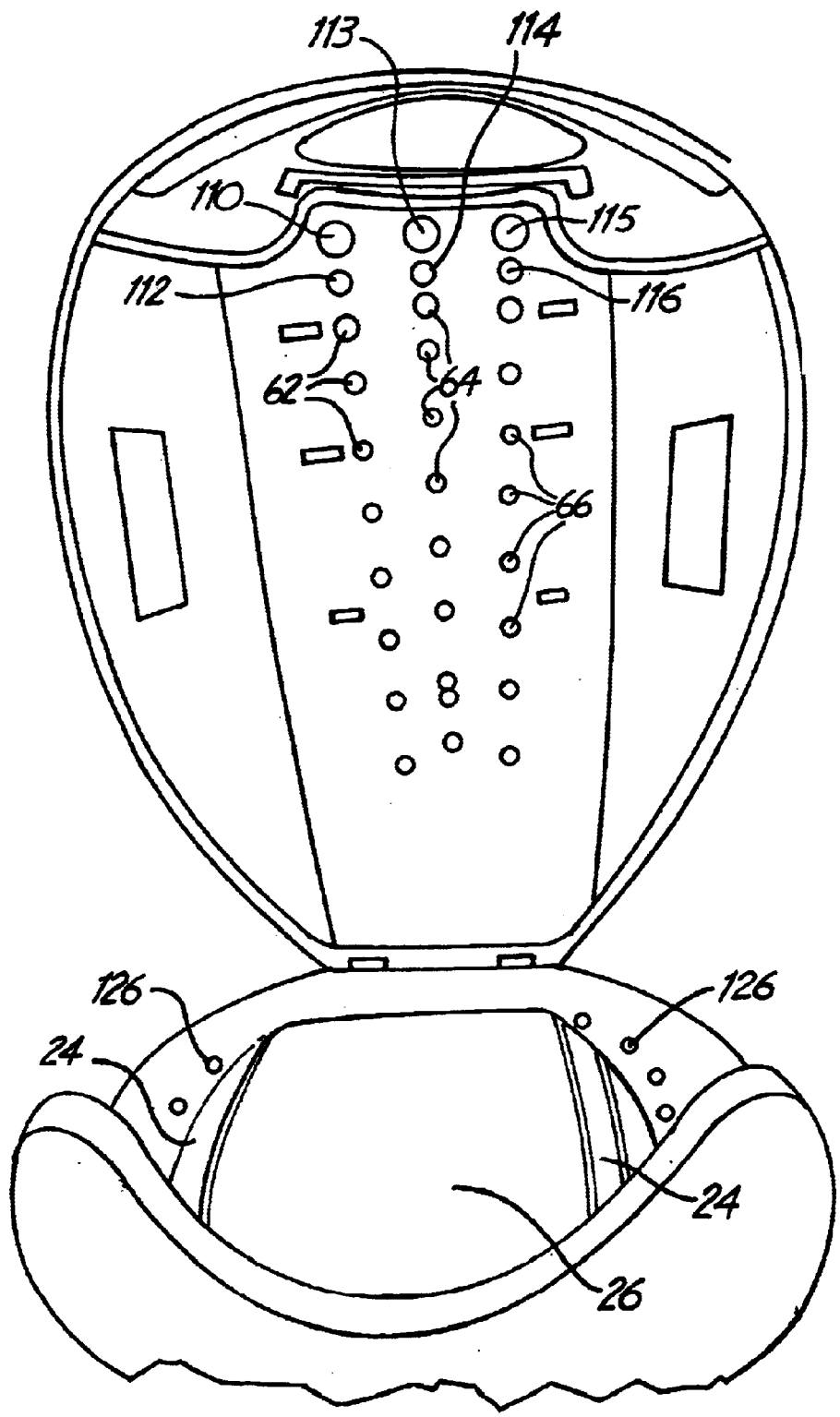
FIG. 5 is an end perspective view from the head end with the cover in open user entry position showing an array of shower nozzles, as well as dry heat outlet openings according to the present invention.

When one of the color of lights is selected, by operating one of a number of switches that are illustrated at 111 in FIG. 4 and at 111A, B, C, D in FIG. 6D, the lights and the color source for the water for a colored shower and the corresponding aroma source 112B, 114B and 116B (FIG. 7) would commence together for complete chromatherapy treatment. If desired, the color source, aroma, and lights can be individually actuated. The switches can be on the divider or control panel 60 as well. The color dispensers 106, 107 and 108, or additional dispensers as desired, could be activated at the same time as the lights for total coordinated colors.

Aromatherapy is provided by a source of a particular aroma, such as lemon as indicated at 112B in FIG. 7, and also a source of lime aroma indicated at 114B. The source 112B is in a nebulizer having a pump 112A that is electrically driven to spray material into the region at the head end of the compartment through a nozzle 113A (FIG. 4). The aroma source can be pressurized if desired so a valve is used for injecting the material where desired. The suitable aroma can be sprayed adjacent to the face of the user, from the nozzle 113A on the panel 60. The additional aroma source 114B shown in FIG. 7 may be lime scent that may require an injector pump, or other type of pump 114A to dispense it out through the nozzle 113A. A manifold can be used to connect the aroma sources with nozzle 113A. A third source 116B can be provided through a pump 116A, or a solenoid valve if it is under pressure, to the nozzle 113A at the head end of the compartment or capsule. The user can make the selection to have the aroma coordinated with the color that is being used in the shower water. Complete therapy involving color and aroma is obtained. The aroma causing liquid can be added to the shower water as well and such source is indicated at 119 in FIG. 7.

The divider or control panel 60 is made to accommodate the necessary controls, which include switches 118 that are operable by the patient or person in the compartment, or the switches can be on the exterior of the base, as illustrated in connection with the switches 111 for the colored lights and water. The panel 60 has a light transmitting window 120 therein, in a suitable location so that a person lying on the bed with her head on the pillow 27 would be able to view the color of the shower water and interior lights, at the same time receiving the scent from the nozzles 113 or from scented shower water. The panel 60 has the switches 50B, 52B and 53B for controlling the valves 50A, 52A and 54A, for the type of shower desired. Control of the temperature, which would include a thermostat control for the inline water heater 75 or the tank heater 76, or both, and other controls, including a drying air control can be on the panel 60.

An air heater 123 and fan 122 are mounted in the foot end of the cover 14 as shown, to provide heated air to duct 124 where the shower water lines extend along the cover 14. Openings 125 direct heated air down onto the person lying on the bed when the person desires to have heated air for drying the body, or for warming the body with the heated air. The fan 122 and heater 123 can be controlled with switch and/or a thermostat in a normal manner. The heater and fan can be mounted in pedestal 18, if desired.

Additionally, a steam generator 127 can be provided in the cavity 30, and steam outlets 126 along the sides of the lower housing just above the gutters can are connected to the steam generator for introducing steam into compartment or chamber 40 from a plurality of such outlets 126. Suitable deflectors can be used for deflecting the steam so that it does not discharge directly upon the person in the compartment.

It should be noted that the bed member 28 can be removed for cleaning and rejuvenation, and waterproof covers can be utilized over the bed cushion to insure that the cushion does not absorb water and become wet, and for sanitary purposes.

Figure 2:
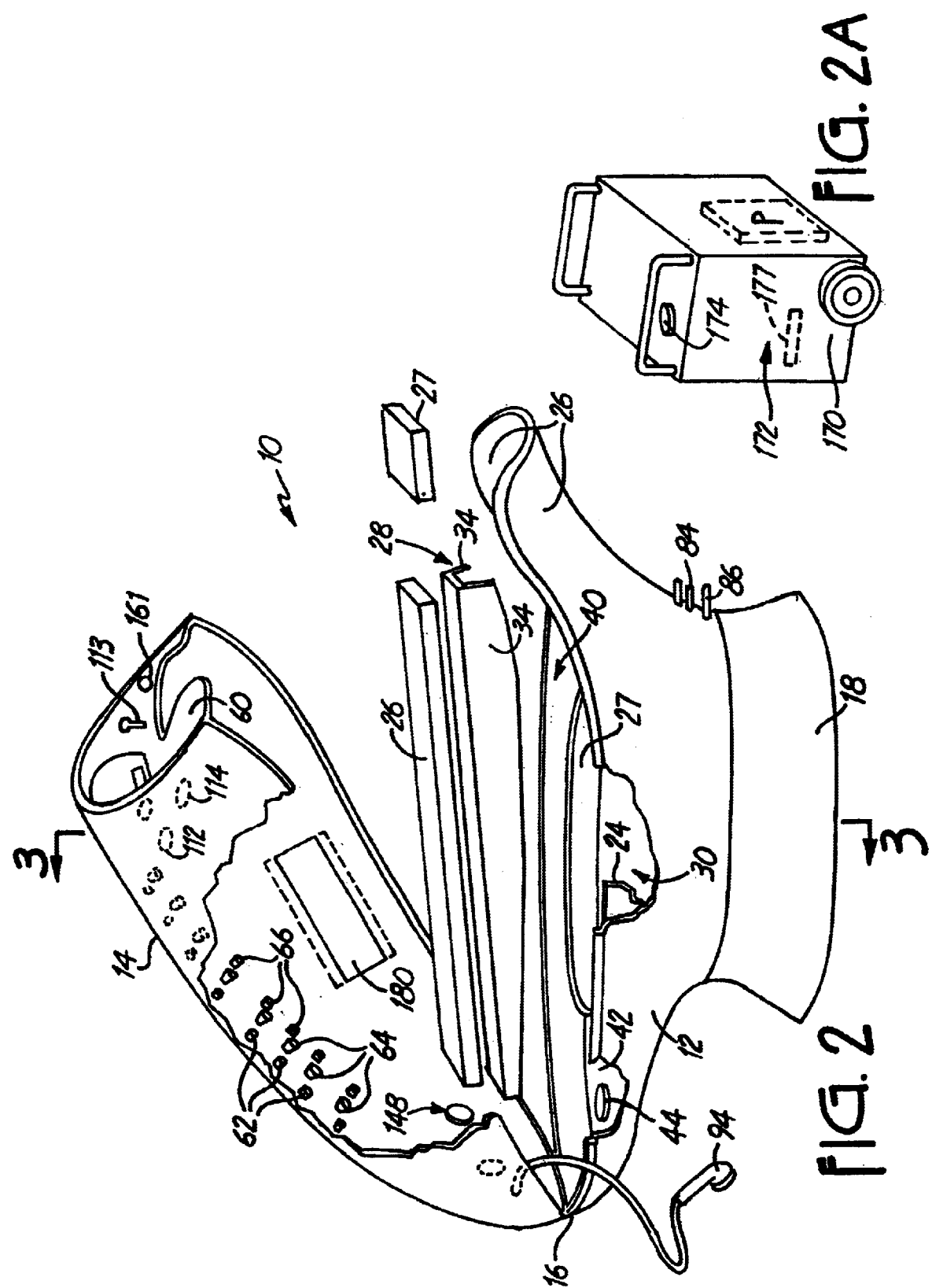
FIG. 2 is a side view with a cover open and parts in exploded position, taken from the opposite side of FIG. 1.

It can also be seen that infrared heat bulbs can be utilized as shown at 148 in FIG. 2, for providing heat as well.

In FIG. 6A, a schematic representation of various controls are shown. The water temperature can be monitored with a suitable thermostat 77, also shown in FIG. 7. Adjustments for the setting of the thermostat can be made with suitable controls indicated at 77A and 77B, and the temperature that is desired is displayed on a screen 77C. Additionally, the solenoid valve switches for selecting the type of shower to have whether the shower water would be from a household or tap supply, the reservoir, or just a cold shower would be selectable with switches 130, 131, and 132 which would control the solenoid valves 102 for example, to insure that the pump 48 is off. When switch 131 is operated, the pump 48 would be turned on and the solenoid 102 would be off as well as the solenoid 91 off. The switch 132 can control a solenoid 91 to turn it on while the others are off.

The shower head solenoid valves 50A, 52A, and 54a are operated with the switches shown at 62S, 64S and 66S for the different types of shower heads.

Additionally, a timer indicated generally at 135 can be installed in the circuit to the pump 48, or to solenoid valves, so that the shower would be on for a selected amount of time. Time adjustment circuit inputs 135A and 135B can be used for adjusting the time that is shown on the display at the timer 135. Manual start and stop buttons illustrated at 138A and 138B also can be provided.

In FIG. 6B, the steam controls are shown. A timer 140 can be used, and a thermostat 142 can be used for selecting the steam temperature or the compartment internal temperature. An on/off switch 143 would control a heater 122A for the steam generator. Timing and temperature can be controlled with suitable adjustment controls 142A and 142B for the temperature, and the timer can be set in the same manner.

FIG. 6C illustrates heat controls. Infrared heat can be provided by ceramic heater such as that shown at 148 in FIG. 2, and these can be controlled with switches 148A that would provide for high, medium or low heat from the infrared sources. Additionally, the fan and blower used for providing dry air heat from the heater and fan 122 and 123 can be controlled with a suitable thermostat control indicated at 150, with the adjustments 150A and 150B used for raising or lowering the compartment temperature, and a straight on/off control 152 also can be provided. The fan and heater would be operated together since when the heater is on the fan should be on. Fan speed also can be controlled as desired.

FIG. 6D, the section of the controls has been explained before, where the light switches are shown for different colored lights, and which can be tied in automatically or manually to the water color and to the aroma source. An optional switch indicated at S can be provided to turn off the automatic control, and manually or automatically operate the water color or aroma sources independently of each other. Additionally, a small fan be provided as shown at 160 in FIG. 1, to provide air out through a face air duct illustrated schematically at 161 in FIG. 2.

FIG. 2A, shows an optional mobile reservoir 170. This mobile reservoir has a tank 172 that has a connection 174 for connecting to the plumbing fittings 82 and 84, as desired. The mobile reservoir can have a pump 175 and an in tank heater 177 for maintaining the temperature in this reservoir tank at a selected level, before being introduced into the shower plumbing of the therapy compartment.

Figure 3:
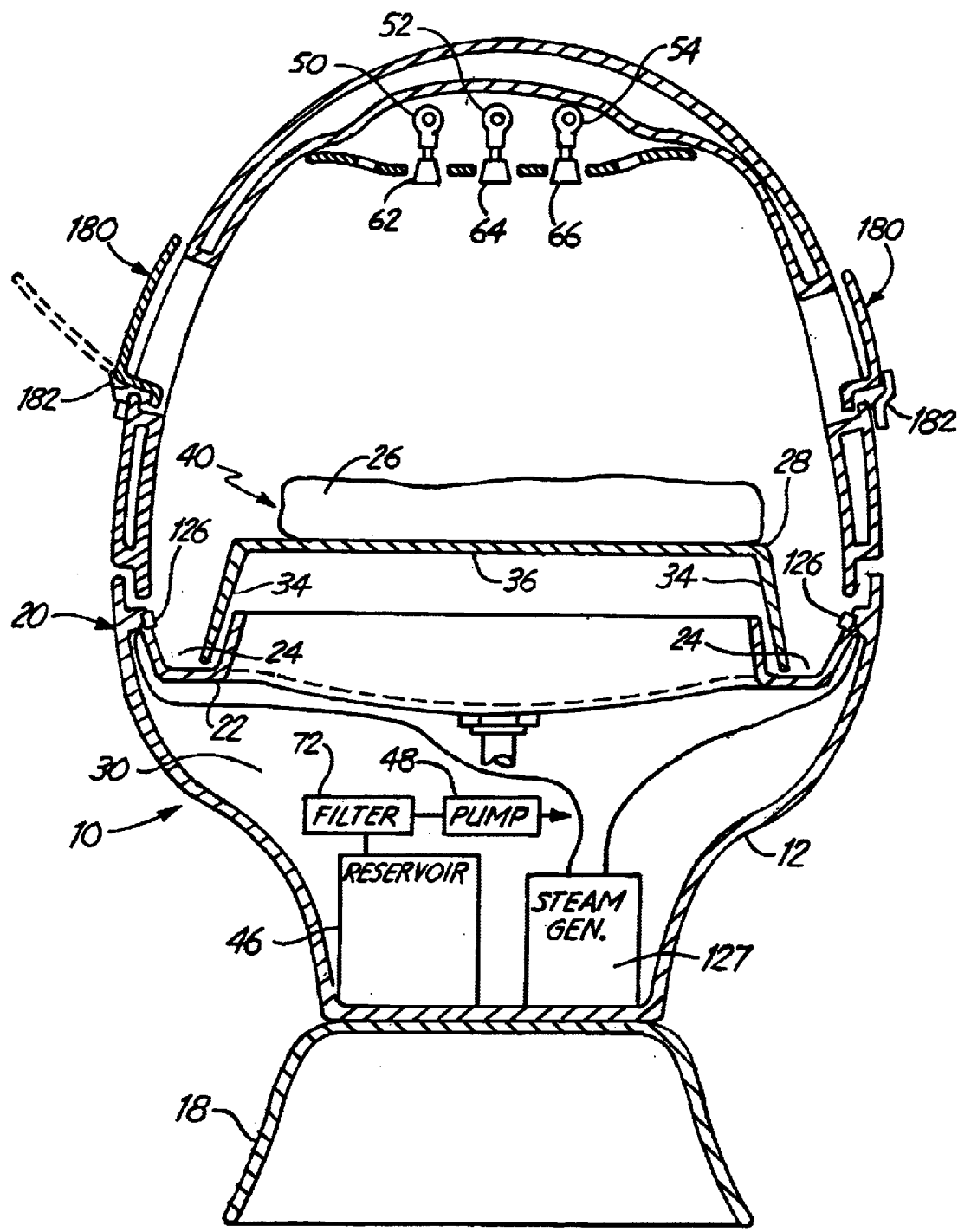
FIG. 3 is a sectional view taken generally along line 3—3 in FIG. 2.

The cover can have panels of a clear material to permit visual inspection on the interior of the compartment, as well as access, for certain treatments of patients. As shown, typical transparent panels are shown at 180, and these are hinged with suitable hinges 182 so that they can be opened as shown in dotted lines in FIG. 3.

Aroma therapy or color therapy has been long recognized as being therapeutic in accordance with many cultures, particularly from India and Asia. The "Chakra" is found in ancient Sanskrit writing, and it represents focal points of energy that are responsive to certain colors. Violet corresponds to the pineal gland, cerebral cortex, right eye, central nervous system, and upper brain function. The brow including the pituitary gland, sinus, nose and sight responds to indigo; the throat, thyroid, lungs and mouth responds to blue; the heart, circulatory system, arms and hands respond to green; the stomach, liver, and pancreas respond to yellow; the sacral area, including reproductive organs respond to orange; and the base of the spine area including kidneys, bladder, legs, etc. respond to red.

Other colors provide therapy to other parts of the body in accordance with the Chakra mind/body connection. The present device provides a method of therapy that coordinates senses of feel, warmth, and color, as well as blending in aroma for a sense of well being and balance. The types of showers can be limitless, for therapy or various combinations.

Figure 8:
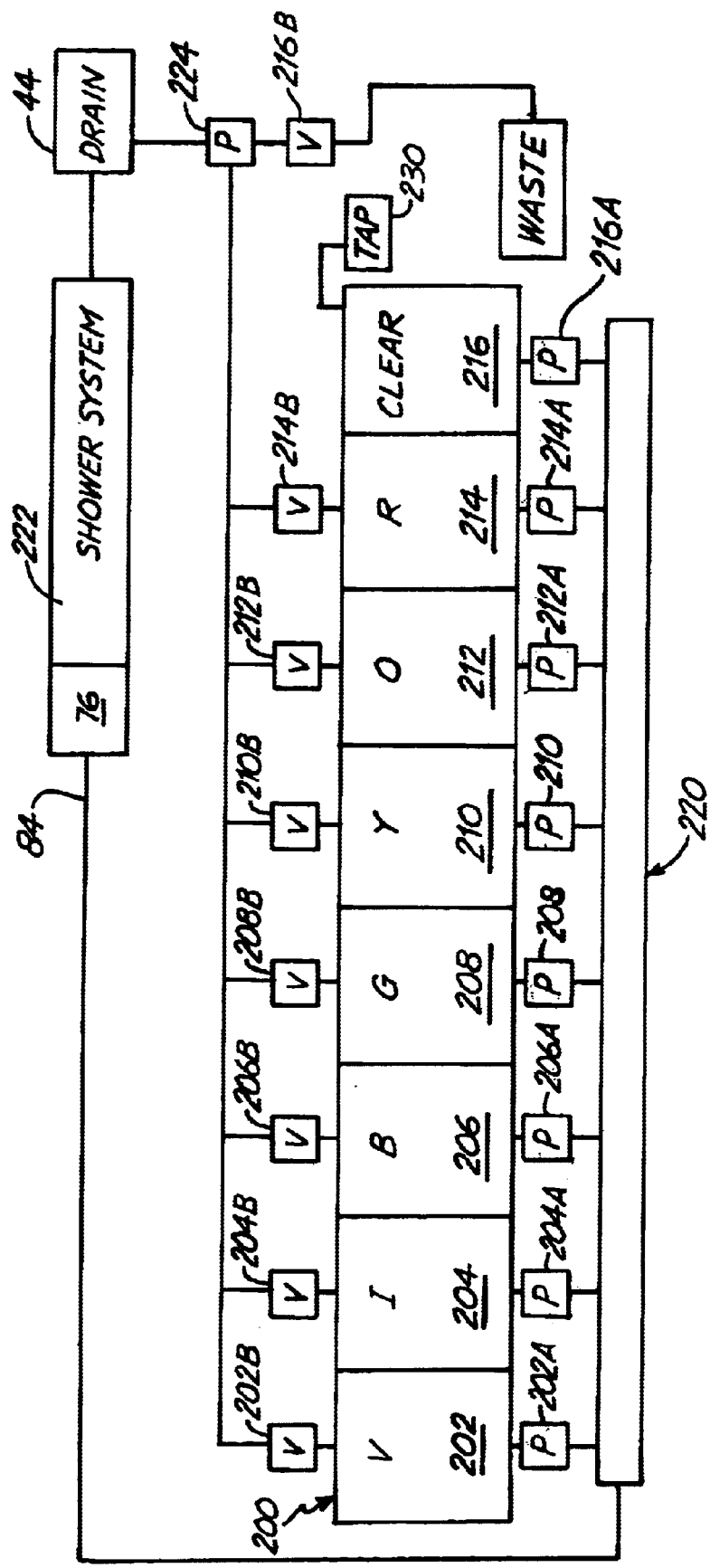
FIG. 8 is a schematic representation of an external multi-compartment, multi-color reservoir for providing a method of sequential color therapy.

In FIG. 8 an auxiliary reservoir 200 has compartments 202 for violet water; 204 for indigo water; 206 for blue water; 208 for green water; 210 for yellow water; 212 for orange water and 214 for red water. A separate tank 216 can be used for clear-flushing water.

Individual pumps can be utilized as shown at 202A, 204A, 206A, 208A, 210A, 212A, 214A, and 216A for individually pumping each of the colored waters through a header or manifold 220 to the shower system shown at 222 that is connected through the manifold 76 as illustrated in the previous drawings on the interior of the compartment. The external fitting 84 can be used, and in this instance, the drain 44 is connected to a pump 224 that will return drain liquids through individual solenoid valves 202B–214B to the individual colored tank being used. Valve 216B is leads to waste or drain. The valves 202B–216B are opened, respectively, when the respective pump is engaged so the drain pump will return the drain water to the proper tank.

For persons practicing color therapy following Chakra teachings, the method would include sequentially providing violet, indigo, blue, green, yellow, orange and red color water, to the shower system indicated at 222 through a connection to header 76, and then being connected through the solenoid valves to each of the shower nozzles or heads previously described.

A clear rinse water can be utilized for cleaning the shower system after each color, if desired. The clear water tank would be recharged each time from a water tap or source 230, and when the clear water has been pumped through the system, the clear water would be pumped to drain through valve 216B from the pump 224. When the color tanks are to be flushed valve 216B will permit directing the waste water to drain.

The method includes sequentially using one or more of the desired Chakra colors for therapy to the respective portions of the body, and if desired rinsing the shower system after each color, and then subsequently following the showering with a different color water.

Again, the controls can be interlocked so that when the pump for the violet unit for example is operated, the solenoid valve from pump 224 would be open to the chamber for the violet water to return to the violet water to that chamber.

The container 200 can have heaters, for maintaining the temperature, and can use inline heaters as previously shown.

The shower system operates independently, and ordinary therapeutic warm showers can be advantageous, as claimed herein, as well as the more detailed method of sequential application of different colors.

The heated air duct is shown in the cover in the drawings, but heated air can be provided from outlet openings alongside the bed, and adjacent the steam outlets, if desired.

Although the present invention has been described with reference to preferred embodiments, workers skilled in the art will recognize that changes may be made in form and detail without departing from the spirit and scope of the invention.

What is claimed is:

1. A method of personalized therapeutic treatment comprising providing a personalized enclosed compartment including a bed, and providing a plurality of shower heads spaced longitudinally along the compartment and overlying the bed, selectively connecting one of the selected number of sources of different colored waters to said shower heads, and sequentially providing each of a plurality of selected different color water through the shower heads by selectively connecting the shower heads to different sources.

2. The method of claim 1, wherein said selected colored water is from the colors consisting of violet, indigo, blue, green, yellow, orange, and red.

3. A personal treatment therapeutic capsule device comprising an elongated generally horizontal compartment of size to hold a person, a bed in the compartment, said bed being oriented substantially horizontally, the compartment having an openable and closeable cover, and a storage space, below the bed, a shower system in the cover comprising a plurality of separate liquid carrying lines extending longitudinally and overlying the bed, a plurality of shower nozzles spaced apart longitudinally on each of the lines to overlie the person on the bed when the cover is closed, and a control for selectively operating the shower system to provide a spray of liquid selectively from each of a plurality of separate liquid sources onto a person on the bed, and each liquid source having a different color from the others.

4. The device of claim 3, wherein there are a plurality of lines carrying shower nozzles in the cover, each of the lines having a different type of a shower nozzle and extending longitudinally to overlie the bed.

5. The device of claim 3, and a source of steam, said source of steam including discharge nozzles on the interior of the compartment adjacent the bed for providing steam on the interior of the compartment at select times.

6. The device of claim 3, including a heater for the sources of water, and a pump for pumping water from the selected source through the lines to the shower nozzles on the lines.

7. The device of claim 3 including a divider panel dividing the compartment into a body containing portion and an exterior head support.

8. The device of claim 7, including a source of heat to provide dry air through openings to the interior of the compartment.

9. The device of claim 7, wherein said divider panel includes a light transmitting portion that is aligned with the head support.

10. The device of claim 3, including selectable colored lights on the interior of the compartment, one of said selectable colored lights and water from a selected source being coordinated to be substantially the same color.

11. The device of claim 10, and a control for simultaneously providing the one selectable colored light and the selected source for the water.

12. The device of claim 10, and a source of an aroma coordinated with the color of the selected source of water and the selectable colored light.

13. The device of claim 12, and a nozzle on a wall of the compartment connected to said source of aroma discharging a scent adjacent the head support.

14. A method of personalized therapeutic treatment comprising providing a personalized enclosed compartment including a bed, and having a headrest portion separated from the compartment and the bed, providing a plurality of water lines along a top of the compartment and a plurality of shower heads spaced longitudinally along each of the lines in the compartment and overlying the bed, providing a plurality of separate sources of water to the lines and each source having a selected color different from colors of the other sources, and selectively providing the colored water from the lines through the associated shower heads toward the bed, and simultaneously providing a light in the compartment substantially the same color as the water discharged from the water lines through the shower heads.

15. The method of claim 14 and selectively providing dry air flowing over the bed.

16. The method of claim 14 and selectively providing steam to the interior of the compartment.

17. The method of claim 14, including heating the water provided to the shower lines.

18. The method of claim 14, including providing an aroma discernible by a user of the compartment that is coordinated with the color of the water discharged from the lines.

19. The method of claim , wherein the providing colored water comprises providing a yellow water, and providing the aroma comprises providing a lemon scent.

20. The method of claim 18, wherein the providing colored water comprises providing green water, green lights, and providing an aroma of a lime fruit.

21. The method of claim 18, wherein providing of colored water comprises providing an orange water, and the providing the aroma comprises providing an aroma of an orange fruit.

22. The method of claim 18, wherein providing colored water comprises providing a color selected from one of violet and indigo, and providing the aroma comprises providing a scent of lavender.

* * * * *

UNITED STATES PATENT AND TRADEMARK OFFICE
CERTIFICATE OF CORRECTION

PATENT NO. : 6,623,511 B1
DATED : September 23, 2003
INVENTOR(S) : Steven J. Daffer, Richard W. Jostrom and Georgios Mertikas It is certified that error appears in the above-identified patent and that said Letters Patent is hereby corrected as shown below:

<u>Column 10,</u>
Line 14, after "claim" insert -- 18 --

Signed and Sealed this

Fifteenth Day of June, 2004

JON W. DUDAS
*Acting Director of the United States Patent and Trademark Office*